US011026874B2

(12) United States Patent
Midori Laga et al.

(10) Patent No.: US 11,026,874 B2
(45) Date of Patent: Jun. 8, 2021

(54) SYSTEMS AND METHODS FOR CHANGING THE COLOR OF HAIR

(71) Applicant: L'OREAL, Paris (FR)

(72) Inventors: Stephanie Midori Laga, Rahway, NJ (US); Shilpa Joshi, Mumbai (IN); Anand Ramchandra Mahadeshwar, Mumbai (IN)

(73) Assignee: L'OREAL, Paris (FR)

(*) Notice: Subject to any disclaimer, the term of this patent is extended or adjusted under 35 U.S.C. 154(b) by 0 days.

(21) Appl. No.: 16/528,140

(22) Filed: Jul. 31, 2019

(65) Prior Publication Data

US 2021/0030653 A1    Feb. 4, 2021

(51) Int. Cl.
*A61Q 5/10* (2006.01)
*A61K 8/49* (2006.01)
*A61K 8/24* (2006.01)
*A61K 8/19* (2006.01)
*A61K 8/365* (2006.01)

(52) U.S. Cl.
CPC .............. *A61K 8/498* (2013.01); *A61K 8/19* (2013.01); *A61K 8/24* (2013.01); *A61K 8/365* (2013.01); *A61Q 5/10* (2013.01); *A61K 2800/884* (2013.01)

(58) Field of Classification Search
CPC ........ A61Q 5/10; A61K 8/19; A61K 2800/88; A61K 2800/4324; A61K 8/347; A61K 8/4973; A61K 2800/884; A61K 8/922; A61K 8/55; A61K 31/215; A61K 8/365; A61K 8/24; A81K 2800/43
USPC ................................................... 8/405, 637.1
See application file for complete search history.

(56) References Cited

U.S. PATENT DOCUMENTS

| | | | |
|---|---|---|---|
| 2,798,053 A | 7/1957 | Brown | |
| 2,923,692 A | 2/1960 | Ackerman et al. | |
| 3,382,607 A | 5/1968 | Ryan et al. | |
| 3,589,978 A | 6/1971 | Kamal et al. | |
| 3,915,921 A | 10/1975 | Schlatzer, Jr. | |
| 4,031,307 A | 6/1977 | DeMartino et al. | |
| 4,131,576 A | 12/1978 | Iovine et al. | |
| 4,237,243 A | 12/1980 | Quack et al. | |
| 4,509,949 A | 4/1985 | Huang et al. | |
| 5,089,578 A | 2/1992 | Valint et al. | |
| 6,241,785 B1 | 6/2001 | Darmenton et al. | |
| 6,312,677 B1* | 11/2001 | Millequant | A61K 8/39 424/401 |
| 6,822,039 B1 | 11/2004 | Monfreux-Gaillard et al. | |
| 8,361,167 B2 | 1/2013 | Blackburn et al. | |
| 2012/0141398 A1 | 6/2012 | Chuang | |

FOREIGN PATENT DOCUMENTS

| | | |
|---|---|---|
| EP | 0173109 A2 | 3/1986 |
| EP | 0503853 A2 | 9/1992 |
| EP | 0750899 A2 | 1/1997 |
| FR | 1441822 A | 6/1966 |
| FR | 2416723 A1 | 9/1979 |
| WO | 98/44012 A1 | 10/1998 |
| WO | 00/31154 A1 | 6/2000 |
| WO | 00/68282 A1 | 11/2000 |

OTHER PUBLICATIONS

Bagda, E., "The relation between surface tension and solubility parameter in liquids," Farbe Lack, 84, 1978, p. 212.
Charron, Craig S., et al., Effect of Dose Size on Bioavailability of Acylated and Nonacylated Anthocyanins from Red cabbage (*Brassica oleracea* L. Var. *capitata*), Journal of Agricultural and Food Chemistry, https://pubs.acs.org/doi/abs/10.1021/jf0710736, May 13, 2019.
Fonnum, G., et al., "Associative Thickeners. Part I: Synthesis, Rheology and Aggregation Behavior," Colloid Polym. Sci., 271, (1993) pp. 380-389.
Hansen, C. M., "Methods of Characterization—Polymers," Hansen Solubility Parameters A User's Handbook, Second Edition, CRC Press LLC, Chapter 5, 2000, pp. 95-111.
Williams, Laurie L., "Determination of Hansen Solubility Parameter Values for Carbon Dioxide," Hansen Solubility Parameters A User's Handbook, Second Edition, CRC Press LLC, Chapter 10, 2000, pp. 177-201.
Khoo et al., "Anthocyanidins and anthocyanins: colored pigments as food, pharmaceutical ingredients, and the potential health benefits," Food & Nutrition Research, 2017, vol. 61, 1361779, https_www.ncbi.nlm.nih, pp. 1-21.
Morishima, Yotaro, "Self-Assembling Amphiphilic Polyelectrolytes and their Nanostructures," Chinese Journal of Polymer Science, vol. 18, No. 40, (2000), pp. 323-336.
Noda, Tetsuya, et al., "Micelle Formation of Random Copolymers of Sodium 2-(Acrylamido)-2-Methylpropanesulphonate and a Nonionic Surfactant Macromonomer in Water as Studied by Fluorescence and Dynamic Light Scattering," Macromolecules 2000, 33, pp. 3694-3704.
Noda, Tetsuya et al., "Solution Properties of Micelle Networks Formed by Nonionic Surfactant Moieties Covalently Bound to a Polyelectrolyte: Salt Effects on Rheological Behavior," Langmuir 2000, 16, pp. 5324-5332.
Noda, Tetsuya, et al., "Stimuli-Responsive Amphiphilic Copolymers of Sodium 2-(Acrylamido)-2-Methylpropanesulphonate and Associative Macromonomers," Polym. Preprint, Div. Polym. Chem. 1999, 40(2), pp. 220-221.

(Continued)

*Primary Examiner* — Eisa B Elhilo
(74) *Attorney, Agent, or Firm* — The Marbury Law Group, PLLC

(57) ABSTRACT

The present disclosure relates to systems, compositions, methods, and kits for coloring hair. The systems comprise at least two compositions: (i) a first composition comprising at least one pigment, and (ii) a second color changing composition comprising at least one color changing agent. The methods comprise changing the color of the hair by applying the first composition (i) onto the hair to change the hair from an initial hair color to a first hair color, and subsequently applying the second composition (ii) onto the hair to change the color of the hair from the first hair color to a second hair color.

28 Claims, No Drawings

(56) References Cited

OTHER PUBLICATIONS

Wiczkowski, Wieslaw et al., "Red cabbage anthocyanins: Profile, isolation, identification, and antioxidant activity," ScienceDirect, Food Research International, vol. 51, Issue 1, Apr. 2013, https://www.sciencedirect.com/science/article/pii/S0963996912005388, retrieved May 13, 2019.

Wu, Xianli et al., "Concentrations of Anthocyanins in Common Foods in the United States and Estimation of Normal Consumption," Journal of Agricultural and Food Chemistry, http://pubs.acs.org/doi/10.1021/0603001, May 13, 019.

Zviak, Charles, "Science Des Traitements Capillaires," [Hair Treatment Science], published by Masson, 1988, pp. 214-279.

* cited by examiner

SYSTEMS AND METHODS FOR CHANGING THE COLOR OF HAIR

TECHNICAL FIELD

The present disclosure relates to systems, compositions, methods, and kits for changing the color of hair.

BACKGROUND

It is known to color hair with permanent, semi-permanent, or temporary hair color compositions. Permanent hair color compositions contain oxidation dye precursors which are colorless or weakly colored compounds which, in combination with oxidizing products, can give rise to colored compounds by an oxidative condensation process. Permanent hair color compositions impart color to the hair that is long lasting and does not wash out.

In contrast, semi-permanent and temporary hair color compositions alter the color of the hair by depositing colored chemicals directly onto the surface of the hair. These so-called "direct dyes" may include nonionic or ionic dyes capable of producing a more or less pronounced change of the natural color of the hair. Semi-permanent hair dyes will gradually wash out over time, generally in about 6-12 washings, and temporary hair color will typically wash out after 1-4 washings. Therefore, consumers may choose a semi-permanent or temporary hair color composition when it is desired to only temporarily alter the color of the hair. Semi-permanent and temporary hair color compositions typically impart monotone color to the hair, and are usually applied at home.

However, consumers today desire to color their hair with non-traditional hair colors such as red, pink, purple, blue, teal, green, etc., to have multiple colors on different portions of their hair, and/or to change the color of their hair frequently. There is, therefore, a need for more convenient, versatile, and customizable hair coloring systems, compositions, and methods, which can be used by a consumer to address these desires.

SUMMARY

The present disclosure relates to compositions, systems, and methods for changing the color of the hair. In at least certain embodiments, the active ingredients of the compositions, systems, and methods are naturally derived.

According to one embodiment, the disclosure relates to systems comprising (i) a first composition comprising at least one pigment, and (ii) a second composition comprising at least one color changing agent, wherein the at least one pigment is capable of imparting a first color to the hair that can be changed to a second hair color by the color changing agent of the second composition, and wherein the pH of the first and second compositions are different.

In further embodiments, the systems for coloring hair comprise (i) a first composition comprising (a) at least one anthocyanin chosen from cyanidin-3-diglucoside-5-glucoside, optionally acylated with p-coumaric, ferulic, or sinapic acids, or combinations thereof, (b) at least one solvent chosen from water and organic solvents, and (c) optionally at least one additional component chosen from cationic surfactants, nonionic surfactants, cationic polymers, fatty compounds, amino silicones, thickeners, solvents, pH adjusters, preservatives, and conditioning agents; and (ii) a second composition comprising: (a) at least one color changing agent chosen from citric acid, sodium phosphate monobasic, sodium citrate, sodium phosphate dibasic, sodium bicarbonate, and sodium carbonate, and (b) at least one solvent chosen from water and organic solvents, wherein the at least one pigment is capable of imparting a first color to the hair that can be changed to a second hair color by the color changing agent of the second composition, and wherein the pH of the first and second compositions are different.

In yet further embodiments, methods of changing the color of the hair comprise (i) applying a first composition comprising at least one pigment to the hair, and (ii) applying a second composition comprising at least one color changing agent to the hair, wherein the hair is rinsed after the application of the first composition and before the application of the second composition, wherein the at least one pigment is capable of imparting a first color to the hair that can be changed to a second hair color by the color changing agent of the second composition, and wherein the pH of the first and second compositions are different.

In still further embodiments, the disclosure relates to kit for changing the color of the hair, the kits comprising (i) a first container comprising a first composition comprising at least one pigment, and (ii) a second container comprising a second composition comprising at least one color changing agent, wherein the at least one pigment is capable of imparting a first color to the hair that can be changed to a second hair color by the color changing agent of the second composition, and wherein the pH of the first and second compositions are different.

DESCRIPTION

The present disclosure relates to systems, compositions, methods, and kits for changing the color of the hair. The systems comprise at least two compositions: (i) a first composition comprising at least one pigment, and (ii) a second color changing composition comprising at least one color changing agent. The methods comprise changing the color of the hair by applying the first composition (i) onto the hair to change the color of the hair from an initial hair color to a first hair color, and subsequently applying the second composition (ii) onto the hair to change the color of the hair from the first hair color to a second hair color.

First Composition

The first composition comprises at least one pigment for changing the color of the hair from an initial hair color to a first hair color. The phrase "initial hair color," and variations thereof, means the color of the hair to which the first composition is applied, before the application thereto. The initial hair color may, for example, be the natural color of the hair, or the hair may have been previously bleached or dyed; thus the initial hair color may be the natural hair color or may be a bleached or dyed color. The phrase "first hair color," and variations thereof, means the color of the hair after the hair color has been changed by application of the first composition. By way of illustrative example only, the initial hair color may be a bleached blonde color, and the application of the first composition thereto may change the color of the hair to a red or pink first hair color.

The at least one pigment for changing the color of the hair may be naturally derived. By "naturally derived," and variations thereof, it is meant that the component is obtained from a natural source, such as a plant or naturally-occurring mineral. The at least one pigment must be capable of imparting a first color to the hair that can be changed to a second hair color by the color changing agent of the second composition.

For example, the at least one pigment may be chosen from anthocyanins, which may be obtained from the leaves, stems, roots, flowers, fruit, etc. of many plants, and derivatives thereof. The basic structure of anthocyanin is shown in formula I:

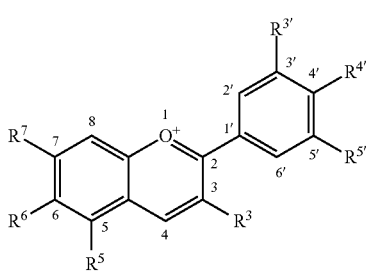

wherein:
R3' may be chosen from —H, —OH, or —OCH3;
R4' may be chosen from —OH;
R5' may be chosen from —H, —OH, or —OCH3;
R3 may be chosen from —OH or —O-sugar, where the sugar is preferably D-glucose, L-rhamnose, D-galactose, D-xylose, or D-arabinose;
R5 may be chosen from —OH or —OCH3;
R6 may be chosen from —H or —OH; and
R7 may be chosen from —OH or —OCH3.

Optionally, anthocyanins useful as the pigment in the first composition may have aromatic phenolic acid substituents such as benzoic acid or cinnamic acid derivatives, or aliphatic organic acid attachments such as malonic, acetic, malic, succinic, or oxalic acids. Acyl substituents may optionally be attached to the C3 sugar.

The anthocyanins may be chosen from, for example, cyanidin, delphinidin, malvidin, pelargonidin, peonidin, or petunidin. In one embodiment, the anthocyanin may comprise cyanidin, e.g. where R3', R4', R5, and R7 are —OH, R5' and R6 are —H, and R3 is —O-glucose. In yet further embodiments, the anthocyanins may comprise cyanidin-3-diglucoside-5-glucoside, optionally acylated with p-coumaric, ferulic, or sinapic acids, or combinations thereof, cyanidin-3-(2"-(2"-sinapoylglucosyl)-6"-sinapoylglucoside)-5-glucoside, cyanidin-3-(2"-glucosylglucoside)-5-glucoside, or cyanidin-3-(2"-('"-sinapoylglucosyl)-6"-sinapoylglucoside)-5-glucoside).

The anthocyanins may be naturally derived. By way of example only, the anthocyanins may be obtained from natural sources such as radishes, purple sweet potatoes, apples, blueberries, raspberries, cranberries, red cabbage, strawberries, eggplant, beets, cherries, curry powder, grapes, onions, peaches, pears, plums, radishes, tomatoes, oranges, purple corn, lingonberries, olives, or turnips, such as from the skin, fruit, leaves, juice, etc., of any of these sources which contains anthocyanins.

It may be possible to extract anthocyanins from natural sources for use in the first compositions of the disclosure by any procedure known in the art, such as by solid phase or solvent extraction. By way of example, the natural source may be soaked in an appropriate solvent for a period of time to extract the anthocyanins, and the solution filtered and treated. By way of example, the natural source of anthocyanins may be soaked in a solvent such as acidified water or ethanol for a period ranging up to about 72 hours, such as up to about 48 hours, up to about 24 hours, up to about 12 hours, or up to about 6 hours, optionally at room temperature or in a cool, dark location or under vacuum. After the desired soaking period, the natural source may be removed from the solvent and the solution may be filtered and/or washed and/or and concentrated, e.g. by boiling. The remaining solution or concentrate may then be used as a pigment for the first composition, for example by being directly added to a hair color base composition or alternatively by being transformed into a powder, e.g. by lyophilization before being added to a hair color base composition.

The at least one pigment, e.g. at least one anthocyanin, may be present in the first composition in a total amount up to about 10%, such as about 0.001% to about 10%, relative to the total weight of the first composition. For example, in various embodiments, the at least one pigment may be present in the first composition in an amount of about 0.001%, about 0.01%, about 0.1%, about 0.5%, about 1%, about 2%, about 3%, about 4%, about 5%, about 6%, about 7%, about 8%, about 9%, or about 10%, or may range from about 0.001% to about 10%, about 0.001% to about 9%, about 0.001% to about 8%, about 0.001% to about 7%, about 0.001% to about 6%, about 0.001% to about 5%, about 0.001% to about 4%, about 0.001% to about 3%, about 0.001% to about 2%, about 0.001% to about 1%, or about 0.001% to about 0.5%, relative to the total weight of the first composition. In further embodiments, the at least one pigment may range from about 0.01% to about 10%, about 0.01% to about 9%, about 0.01% to about 8%, about 0.01% to about 7%, about 0.01% to about 6%, about 0.01% to about 5%, about 0.01% to about 4%, about 0.01% to about 3%, about 0.01% to about 2%, or about 0.01% to about 1%, relative to the total weight of the first composition.

The first composition further comprises additional components useful in a hair color composition. Any traditional components for a hair color composition may be chosen, so long as they do not substantially interfere with the goal of imparting a first color to the hair to which the first composition is applied.

By way of example, the first composition may comprise at least one cationic surfactant. The cationic surfactants may, for example, be chosen from primary, secondary or tertiary fatty amines, which are optionally polyoxyalkylenated, or salts thereof, and quaternary ammonium salts, and mixtures thereof.

The fatty amines generally comprise at least one $C_8$-$C_{30}$ hydrocarbon-based chain. Non-limiting examples of quaternary ammonium salts that may be used include those corresponding to the following general formula (VI):

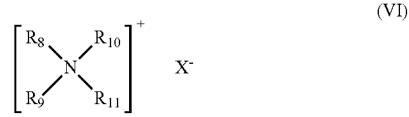

wherein:
the groups R8 to R11, which may be identical or different, represent a linear or branched aliphatic group comprising from 1 to 30 carbon atoms, or an aromatic group such as aryl or alkylaryl, at least one of the groups R8 to R11 denoting a linear or branched aliphatic radical comprising from 8 to 30 carbon atoms, preferably from 12 to 24 carbon atoms; and
X is an anion chosen from the group of halides, phosphates, acetates, lactates, ($C_1$-$C_4$)alkyl sulfates, ($C_1$-$C_4$) alkylsulfonates and ($C_1$-$C_4$)alkylarylsulfonates.

In at least certain embodiments, the aliphatic groups may comprise heteroatoms such as oxygen, nitrogen, sulfur and halogens. The aliphatic groups may be chosen, for example, from $C_1$-$C_{30}$ alkyl, $C_1$-$C_{30}$ alkoxy, ($C_2$-$C_6$) polyoxyalkylene, $C_1$-$C_{30}$ alkylamide, ($C_{12}$-$C_{22}$)alkylamido($C_2$-$C_6$)alkyl, ($C_{12}$-$C_{22}$)alkyl acetate, and $C_1$-$C_{30}$ hydroxyalkyl groups.

Among the quaternary ammonium salts of formula (VI), tetraalkyl-ammonium salts, for instance dialkyldimethylammonium or alkyltrimethylammonium salts in which the alkyl group comprises approximately from 12 to 22 carbon atoms, in particular behenyltrimethylammonium, distearyldimethylammonium, cetyltrimethylammonium or benzyldimethylstearylammonium salts, may be chosen. Further, the palmitylamidopropyltrimethylammonium salts, the stearamidopropyltrimethylammonium salts, the stearamidopropyldimethylcetearylammonium salts, or the stearamidopropyl-dimethyl(myristyl acetate)ammonium salts, such as those sold under the name Ceraphyl® 70 by the company Van Dyk, may be chosen. It is preferred in particular to use the chloride salts of these compounds. For example, behenyltrimethylammonium chloride and/or cetyltrimethylammonium chloride may be chosen.

The at least one cationic surfactant may be present in the first composition in an amount ranging from about 0.1% to about 6% by weight, relative to the total weight of the first composition, such as from about 0.5% to about 5%, about 0.5% to about 4%, or about 1% to about 3% by weight, for example about 1% to about 2% by weight of the first composition.

The first composition may further comprise at least one nonionic surfactant. By way of non-limiting example only, nonionic surfactants may advantageously be chosen from alkyl ethers and alkyl esters of polyalkylene glycol, in particular of polyethylene glycol. For example, polyethylene glycol octyl ether, polyethylene glycol lauryl ether, polyethylene glycol tridecyl ether, polyethylene glycol cetyl ether, and polyethylene glycol stearyl ether may be chosen, such as trideceth-3, trideceth-10, and/or trideceth-6.

Further exemplary and non-limiting nonionic surfactants comprise polyethylene glycol nonylphenyl ether, polyethylene glycol dodecylphenyl ether, polyethylene glycol cetylphenyl ether, polyethylene glycol stearylphenyl ether, polyethylene glycol sorbitan monostearate, polyethylene glycol sorbitan monooleate, polyethylene glycol stearate, e.g. PEG-100 stearate.

The at least one nonionic surfactant may be present in the first composition in an amount ranging from about 0.01% to about 2% by weight, relative to the total weight of the first composition, such as from about 0.05% to about 2%, about 0.05% to about 1%, or about 0.05% to about 0.5% by weight, for example about 0.05% to about 0.3%, such as about 0.1%, by weight of the first composition.

In certain embodiments, the first composition may further comprise at least one cationic polymer, which may impart benefits such as softening and sheen to the hair. As used herein, the term "cationic polymer" denotes any polymer containing cationic groups and/or groups that may be ionized into cationic groups. By way of non-limiting example, the cationic polymers may be chosen from those containing units comprising primary, secondary, tertiary and/or quaternary amine groups, which may either form part of the main polymer chain or may be borne by a side substituent directly attached thereto. Among the cationic polymers that may be mentioned more particularly are polymers of the polyamine, polyamino amide and polyquaternary ammonium type.

By way of non-limiting example, cationic cellulose derivatives such as the copolymers of cellulose or cellulose derivatives grafted with a water-soluble quaternary ammonium monomer, described especially in U.S. Pat. No. 4,131,576, such as hydroxyalkylcelluloses, for instance hydroxymethyl-, hydroxyethyl-, or hydroxypropylcelluloses grafted especially with a methacryloylethyltrimethylammonium, methacrylamidopropyltrimethylammonium, or dimethyldiallylammonium salt. The commercial products corresponding to this definition are more particularly the products sold under the name Celquat L 200 and Celquat H 100 by the company Akzo Nobel.

The cationic guar gums described more particularly in U.S. Pat. Nos. 3,589,578 and 4,031,307, such as guar gums containing trialkylammonium cationic groups. For example, guar gums modified with a salt (e.g., chloride) of 2,3-epoxypropyltrimethylammonium, may be used. Mention may be made of guar hydroxypropyltrimonium chloride and hydroxypropyl guarhydroxypropyl trimonium chloride, such as those sold especially under the trade names Jaguar C13S, Jaguar CHS, Jaguar CI7, and Jaguar CI62 by the company Solvay.

The cationic polymer may be present in the first composition in an amount ranging from about 0.01% to about 2% by weight, relative to the total weight of the first composition, such as from about 0.05% to about 2%, about 0.05% to about 1%, or about 0.05% to about 0.5% by weight, for example about 0.05% to about 0.3%, such as about 0.1%, by weight of the first composition.

The first composition may optionally further comprise one or more fatty compounds. Non-limiting examples of fatty compounds include oils, mineral oil, fatty alcohols, fatty acids, fatty alcohol derivatives, fatty acid derivatives (such as alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), esters of fatty alcohols, hydroxyl substituted fatty acids, waxes, triglyceride compounds, lanolin, and a mixture thereof. For instance, one or more fatty compounds may be selected from the group consisting of ozokerite, cetearyl alcohol, tribehenin, stearyl alcohol, petrolatum, C12-C14 isoparaffin, C12-C15 alkylbenzoate, and a mixture thereof.

Fatty alcohols useful herein include those having from about 10 to about 30 carbon atoms, such as from about 12 to about 22 carbon atoms, or from about 16 to about 22 carbon atoms. These fatty alcohols can be straight or branched chain alcohols and can be saturated or unsaturated. Nonlimiting examples of fatty alcohols include decyl alcohol, undecyl alcohol, dodecyl, myristyl, cetyl alcohol, stearyl alcohol, isostearyl alcohol, isocetyl alcohol, behenyl alcohol, linalool, oleyl alcohol, cholesterol, cis4-t-butylcyclohexanol, myricyl alcohol and a mixture thereof. In some cases, the fatty alcohols are those selected from the group consisting of cetyl alcohol, stearyl alcohol, cetearyl alcohol, isostearyl alcohol, oleyl alcohol, and a mixture thereof.

Fatty acids useful herein include those having from about 6 to about 30 carbon atoms, from about 10 to about 22 carbon atoms, and from about 12 to about 22 carbon atoms. These fatty acids can be straight or branched chain acids and can be saturated or unsaturated. Also included are diacids, triacids, and other multiple acids which meet the carbon number requirement herein. Also included herein are salts of these fatty acids. Nonlimiting examples of fatty acids include lauric acid, palmitic acid, stearic acid, behenic acid, arichidonic acid, oleic acid, isostearic acid, sebacic acid, and a mixture thereof. In some cases, the fatty acids are selected from the group consisting of palmitic acid, stearic acid, and a mixture thereof.

Fatty alcohol derivatives include alkyl ethers of fatty alcohols, alkoxylated fatty alcohols, alkyl ethers of alkoxylated fatty alcohols, esters of fatty alcohols and a mixture thereof. Non-limiting examples of fatty alcohol derivatives include materials such as methyl stearyl ether; 2-ethylhexyl dodecyl ether; stearyl acetate; cetyl propionate; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through 10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG-8-ceteth-1, and PPG-10 cetyl ether; and a mixture thereof.

The first composition may optionally also comprise at least one amino silicone. As used herein, the term "amino silicone" denotes a silicone comprising at least one primary, secondary, or tertiary amine, or quaternary ammonium. In various embodiments, the amino silicones may be chosen from those of formula (II):

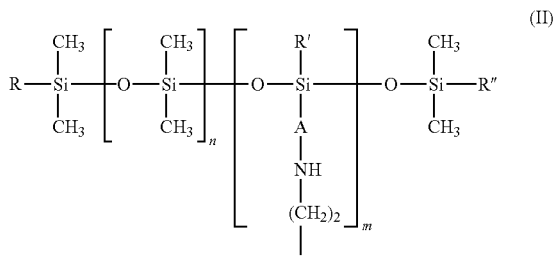

wherein:
R, R', and R'', which may be identical or different, denote a C1-C4 alkyl, optionally CH3, radical, a C1-C4 alkoxy, optionally methoxy, radical or an —OH radical;
A represents a linear or branched C3-C8, optionally C3-C6, alkylene radical; and
m and n are integers which depend on the molecular weight and the sum of which is between 1 and 2000.

By way of non-limiting example, in one embodiment R, R', and R'', which may be identical or different, represent a C1-C4 alkyl, preferably methyl, radical or a hydroxyl radical, A represents a C1-C8, preferably C3-C4, alkylene radical, and m and n are chosen such that the weight-average molecular weight of the compound ranges from about 5000 to about 500,000. The compounds of this type are named "amodimethicone" in the CTFA dictionary.

By way of further non-limiting example, R, R' and R'', which may be identical or different, represent a $C_1$-$C_4$ alkoxy or hydroxyl radical, at least one of the R or R'' radicals is an alkoxy radical, and A represents a $C_3$ alkylene radical. The hydroxyl/alkoxy mole ratio may be between 0.2/1 and 0.4/1, and for example equal to 0.3/1. Moreover, m and n are chosen such that the weight-average molecular weight of the compound ranges from about 2000 to about $1 \times 10^6$. More particularly, n ranges from 0 to 999 and m ranges from 1 and 1000, the sum of n and m ranging from 1 to 1000. For example, the product Belsil® ADM 652 sold by Wacker may be used.

By way of yet a further non-limiting example, R and R'', which may be identical or different, represent a C1-C4 alkoxy or hydroxyl radical, wherein at least one of the R and R'' radicals is an alkoxy radical, R' represents a methyl radical, and A represents a C3 alkylene radical. The hydroxyl/alkoxy mole ratio may range from 1/0.8 to 1/1.1, for example may be equal to 1/0.95. Moreover, m and n are chosen such that the weight-average molecular weight of the compound ranges from about 2000 to about 200,000. More particularly, n ranges from 0 to 999 and m ranges from 1 to 1000, the sum of n and m ranging from 1 to 1000. For example, the product Fluid WR® 1300 sold by Wacker may be used.

The first composition may further comprise at least one thickener. For example, water-soluble or water-dispersible thickening polymers may be used. The thickeners may in particular be chosen from homopolymers or copolymers of acrylic or methacrylic acids and/or of salts and/or esters thereof, such as crosslinked copolymers of acrylic acid and/or methacrylic acid and of an ester thereof comprising less than 6 carbon atoms, preferably a Ci-$C_4$ alkyl ester, and such as the copolymer sold under the commercial name ACULYN 33® by the company THE DOW CHEMICAL COMPANY and having the INCI name: ACRYLATES COPOLYMER, and the copolymer sold under the commercial name CARBOPOL AQUA SF-1 POLYMER® by the company LUBRIZOL and having the INCI name: ACRYLATES COPOLYMER copolymers of acrylic acid and of acrylamide or the salts thereof, vinyl polymers, such as polyvinylpyrrolidone, copolymers of methyl vinyl ether and of malic anhydride, copolymers of vinyl acetate and of crotonic acid, copolymers of vinylpyrrolidone and of vinyl acetate, copolymers of vinylpyrrolidone and of caprolactam, polyvinyl alcohol, modified or unmodified carboxyvinyl polymers, such as the products sold under the name Carbopol® (CTFA name: carbomer) by the company Goodrich; polyacrylamides; polysaccharide biopolymers, for instance xanthan gum, guar gum, gum Arabic, locust bean gum, acacia gum, scleroglucans, chitin derivatives and chitosan derivatives, carrageenans, gellans, alginates, or celluloses such as microcrystalline cellulose, carboxymethylcellulose, hydroxymethylcellulose, hydroxyethylcellulose, hydroxypropylcellulose, and hydroxypropyl methylcellulose. Mention may be made of, for example, xanthan gum sold under the trade name Keltrol® CG-T by the company CP Kelco and hydroxypropyl methylcellulose such as the product sold under the trade name Benecel K100M Hydroxypropylmethyl Cellulose® by the company Ashland.

The first composition may also comprise additional components such as water and/or other cosmetically acceptable solvents. For example, the first composition may comprise water in an amount up to about 98% by weight, such as up to about 95% by weight, up to about 90% by weight, or up to about 85% by weight, such as from about 80% to about 98%, about 85% to about 95%, or about 88% to about 92% by weight of the first composition.

The first composition may further comprise at least one cosmetically acceptable solvent in an amount ranging from about 0.01% to about 5%, such as about 0.1% to about 3%, about 0.1% to about 2%, or about 0.1% to about 1%, by weight of the first composition. For example, the at least one cosmetically acceptable solvent may, for example, be chosen from volatile or non-volatile organic solvents. As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin.

The first composition may also comprise one or more pH adjusters such as hydrochloric acid, (ortho)phosphoric acid, sulfuric acid, boric acid, or carboxylic acids such as acetic acid, lactic acid, or citric acid, or sulfonic acids.

The pH adjusters may be present in an amount needed to adjust the pH of the composition to the desired pH, such as up to about 1%, up to about 0.5% up to about 0.1%, or from about 0.001% to about 1%, about 0.01% to about 1%, or about 0.01% to about 0.5% by weight of the first composition. The pH of the first composition may range from about 2.5 to about 4.5, such as about 3 to about 4, or about 3.5.

The first composition may also comprise at least one preservative. For example, preservatives may include, but are not limited to, glycerin containing compounds (e.g., glycerin or ethylhexylglycerin or phenoxyethanol), benzyl alcohol, parabens (methylparaben, ethylparaben, propylparaben, butylparaben, isobutylparaben, etc.), sodium benzoate, benzoic acid, chlorhexidine digluconate, ethylenediamine-tetraacetic acid ("EDTA"), potassium sorbate, and/or grapefruit seed extract, or a mixture thereof. Other preservatives are known in the cosmetics industries and include salicylic acid, DMDM Hydantoin, Formaldahyde, Chlorphenism, Triclosan, Imidazolidinyl Urea, Diazolidinyl Urea, Sorbic Acid, Methylisothiazolinone, Sodium Dehydroacetate, Dehydroacetic Acid, Quaternium-15, Stearalkonium Chloride, Zinc Pyrithione, Sodium Metabisulfite, 2-Bromo-2-Nitropropane, Chlorhexidine Digluconate, Polyaminopropyl biguanide, Benzalkonium Chloride, Sodium Sulfite, Sodium Salicylate, Citric Acid, Neem Oil, Essential Oils (various), Lactic Acid, Vitamin E (tocopherol), and a mixture thereof. By way of example only, the first composition may include one or more preservatives selected from the group consisting of sodium benzoate, benzoic acid, chlorhexidinedigluconate, chlorhexidine dihydrochloride, salicylic acid, phenoxyethanol, methyl paraben, or a mixture thereof.

The total amount of preservatives may vary. For example, the preservative may be present in the first composition in an amount ranging from about 0.01% to about 5% by weight, such as about 0.01% to about 3%, about 0.01% to about 1%, or about 0.025% to about 0.075% by weight of the first composition.

Color Changing Composition

The second composition, also referred to herein as a "color changing" composition, comprises at least one agent for changing the color of the hair from the first hair color to a second hair color. The phrase "second hair color," and variations thereof, means the color of the hair after the hair color has been changed from the first hair color by application of the second composition. By way of illustrative example only, the first hair color may be a red or pink color, and application of the second composition may change the color of the hair to a purple, blue, or teal color.

The second composition may have a pH different than that of the first composition. For example, the second composition may have a pH slightly or significantly higher, or slightly or significantly lower, than that of the first composition. In various embodiments, the second composition may have a pH that is up to about 0.5, up to about 1, up to about 1.5, up to about 2, up to about 2.5, or up to about 3 pH units higher or lower than that of the first composition. In other embodiments, the second composition may have a pH that is about 0.5, about 1, about 1.5, about 2, about 2.5, or about 3 pH units higher or lower than that of the first composition. The second composition comprising the color changing agent may thus, in at least certain embodiments, cause the first hair color to change to the second hair color upon application, due to the difference in pH. Thus, the at least one color changing agent may be chosen from acidic or basic components which may optionally be naturally derived.

For example, mineral salts such as carbonates, hydrogen carbonates, sulfates, hydrogen phosphates, and phosphates of alkali metals and alkali earth metals may be used. The inorganic bases that may be used may be chosen from alkali metal phosphates and carbonates such as, for example, sodium phosphate, potassium phosphate, sodium carbonate, sodium bicarbonate, potassium carbonate, potassium bicarbonate, or their derivatives. The inorganic bases may also include alkali metals of carboxylates such as, for example, sodium acetate, potassium acetate, sodium citrate, potassium citrate, or their derivatives.

In further embodiments, the at least one color changing agent may be chosen from mineral or organic acids such as hydrochloric acid, ortho-phosphoric acid, sulfuric acid, carboxylic acids such as acetic acid, tartaric acid, citric acid, glycolic acid, and lactic acid, sulfonic acids, or a combination of glycine and hydrochloric acid. By way of non-limiting example only, the at least one color changing agent may be chosen from citric acid, sodium phosphate monobasic, sodium citrate, sodium phosphate dibasic, sodium bicarbonate, and sodium carbonate.

The at least one color changing agent may be present in the second composition in a total amount up to about 10%, such as about 0.001% to about 10%, relative to the total weight of the second composition. For example, in various embodiments, the at least one color changing agent may be present in the second composition in an amount of about 0.001%, about 0.01%, about 0.1%, about 0.5%, about 1%, about 2%, about 3%, about 4%, about 5%, about 6%, about 7%, about 8%, about 9%, or about 10%, or may range from about 0.001% to about 10%, about 0.001% to about 9%, about 0.001% to about 8%, about 0.001% to about 7%, about 0.001% to about 6%, about 0.001% to about 5%, about 0.001% to about 4%, about 0.001% to about 3%, about 0.001% to about 2%, about 0.001% to about 1%, or about 0.001% to about 0.5%, relative to the total weight of the second composition. In further embodiments, the at least one color changing agent may range from about 0.01% to about 10%, about 0.01% to about 9%, about 0.01% to about 8%, about 0.01% to about 7%, about 0.01% to about 6%, about 0.01% to about 5%, about 0.01% to about 4%, about 0.01% to about 3%, about 0.01% to about 2%, or about 0.01% to about 1%, relative to the total weight of the second composition.

The second composition further comprises at least one solvent chosen from water and organic solvents and mixtures thereof. The organic solvents may be volatile or non-volatile compounds. As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin.

The at least one solvent may be present in the composition in an amount ranging up to about 99.9% by weight of the second composition. For example, the at least one solvent may be present in the composition in an amount ranging from about 80% to about 99.9%, about 85% to about 99%, about 90% to about 98%, about 92% to about 98%, or about 94% to about 97%, by weight of the second composition.

In various embodiments, the second composition may have a concentration of color-changing agent (in the solvent(s)) up to about 1000 mM, such as up to about 900 mM, up to about 800 mM, up to about 700 mM, up to about 600 mM, or up to about 500 mM, for example ranging from about 1 mM to about 500 mM, from about 5 mM to about 400 mM, from about 10 mM to about 300 mM, from about 20 mM to about 200 mM, from about 50 mM to about 150 mM, or from about 75 mM to about 125 mM. As further examples, the concentration may be about 1 mM, about 10 mM, about 20 mM, about 50 mM, about 60 mM, about 70 mM, about 75 mM, about 80 mM, about 85 mM, about 90 mM, about 95 mM, about 100 mM, about 105 mM, about 110 mM, about 115, mM, about 120 mM, about 125 mM, about 130 mM, about 140 mM, about 150 mM, about 200 mM, about 225 mM, about 250 mM, about 275 mM, about 300 mM, about 325 mM, about 350 mM, about 375 mM, about 400 mM, about 450 mM, or about 500 mM.

The color changing agent may, for example, be in powder or liquid form before it is combined with the at least one solvent.

Additional Components

Either the first or second composition, or both, may comprise additional components, provided they do not substantially interfere with the ability of the composition to alter the color of the hair as described herein. In certain embodiments, the additional components may provide textural benefits to the composition and/or the hair.

These additional components may be chosen from, for example, anionic polymers, nonionic polymers, rheology modifiers, thickening and/or viscosity modifying agents, associative or non-associative polymeric thickeners, non-polymeric thickeners, non-polymeric cationic surfactants, nacreous agents, dyes or pigments, fragrances, minerals, plant or synthetic oils, waxes, fatty alcohols, lipids, vitamins, proteins including ceramides, vitamins, UV-screening agents, free-radical scavengers, preserving agents, pH stabilizers, conditioning agents, smoothing agents, and mixtures thereof.

The additional component(s) may be present in a total combined amount up to about 90%, such as up to about 80%, up to about 70%, up to about 60%, up to about 50%, up to about 40%, up to about 30%, up to about 20%, up to about 10%, or up to about 5% by weight, relative to the total weight of the first or second composition.

Systems for Changing the Color of the Hair

The systems according to the disclosure comprise at least one first composition and at least one second color changing composition. The systems may, in certain embodiments, comprise more than one first composition and/or more than one second composition. As used herein, when the systems comprise more than one second composition for changing the color of the hair, the color changing compositions may be referred to as a second composition, a third composition, a fourth composition, etc., for ease of reference only, and without intending to be limiting.

The systems and compositions can be used to change the color of the hair from an initial hair color to a first hair color and subsequently to a second hair color by application of the first composition followed by application of the second composition. Additionally, systems according to the disclosure may comprise alternate or additional color changing compositions (e.g. a third composition, etc.) containing a different color changing agent than the second composition, which may allow the color change to be reversible or allow the consumer to change the color of the hair to yet a third color, to have multiple colors, and so on. The systems and compositions therefore allow consumers to quickly change the color of their hair, to impart reversible color, and to impart multiple colors to the hair, thus allowing the consumer to customize the color of their hair.

Methods of Changing the Color of the Hair

Methods according to the disclosure comprise applying a first composition comprising at least one pigment to either washed or unwashed hair, leaving the first composition on the hair for a leave-in period, rinsing the hair, and subsequently applying a second color changing composition comprising at least one color changing agent to the hair.

In one embodiment, the color of the hair may be changed from an initial hair color to a first hair color by applying a first composition according to the disclosure to wet or dry hair. The first composition may be in ready-to-use form, e.g. where it already contains the pigment, or the first composition may be prepared by the user by adding a pigment to a hair color base before the composition is applied to the hair.

The first composition may be in the form of a liquid, a gel, a cream, a paste, or the like. The first composition may, for example, be contained in a bottle, a tube, or the like. The first composition may be applied to the hair using traditional techniques for applying a hair color composition, e.g. with a dye brush applicator, a spray bottle, or the like.

After it is applied, the first composition containing at least one pigment may be left on the hair for a leave-in period. For example, the first composition may be left on the hair for up to about two hours, such as up to about 60 minutes, up to about 45 minutes, up to about 30 minutes, up to about 20 minutes, up to about 10 minutes, or up to about 5 minutes. It will be understood that the longer the first composition is left on the hair, the darker the coloration of the hair fibers will be. In various embodiments, the first composition may be left on the hair from about 1 minute to about two hours, such as about 5 minutes to about 60 minutes, about 10 minutes to about 50 minutes, about 20 minutes to about 40 minutes, or about 25 minutes to about 35 minutes, such as about 30 minutes.

After the leave-in period, the first composition may be rinsed from the hair. Optionally, the hair may also be washed and/or conditioned and/or partially or completely dried after the first composition is rinsed from the hair.

After the first composition is rinsed from the hair and the hair is optionally washed and/or conditioned and/or dried, a color changing second composition may be applied to the hair in order to change the color of the hair from the first hair color imparted by the first composition to a second hair color. The second composition may be in ready-to-use form, where it already contains a color changing agent, or the second composition may be prepared by the user by adding a color changing agent to a solvent (e.g. water or an organic solvent) before the composition is applied to the hair.

The second composition may be in the form of a liquid, a gel, a cream, a paste, or the like. The second composition may, for example, be contained in a bottle, a tube, or the like. The second composition may be applied to the hair using traditional techniques for applying a hair color composition, e.g. with a dye brush applicator, a spray bottle, or the like. For example, in an exemplary embodiment the second, color-changing composition may be in the form of an aqueous liquid in a spray bottle (e.g. prepared by mixing an appropriate amount of solid, powdered color changing agent with an appropriate amount of water), and applied with a pump-style spray bottle. In one exemplary embodiment, the aqueous color changing composition may be prepared in a concentration of about 100 mM, and applied by pumping approximately 1-20 pumps, such as 5-15 pumps, or about 10 pumps of the aqueous solution onto the hair. In another exemplary embodiment, the aqueous color changing composition may be prepared in a concentration of about 500 mM, and applied by pumping approximately 1-10 pumps, such as 1-5 pumps, or about 1-2 pumps onto the hair.

It is to be understood that the color changing composition (e.g. the second composition or the third composition, etc.) may be applied to the hair immediately after or substantially immediately after the first composition is rinsed from the hair and the hair is optionally washed and/or conditioned and/or dried, although the consumer may wish to wait for a period of time, e.g. one or more hours or one or more days, before applying a color changing second composition.

The methods according to the disclosure may be useful for consumers to customize the color of their hair. By way of illustrative example only, a user may apply a first composition comprising an anthocyanin obtained from red cabbage to the entire head of hair and leave the composition on the hair for a leave-in period ranging from about 20 minutes to about 40 minutes, in order to change the color of the hair from the initial hair color to a first hair color which is pink or red. After the leave-in period, the user may rinse the first composition from the hair and optionally wash and/or condition and/or dry the hair. If the user wishes to change part or all of the hair to a different color, a color changing second composition can be applied to the portion of the hair where the different color is desired. For example, the user may choose to apply a second composition comprising sodium phosphate dibasic to the middle portion of the hair, e.g. with a pump spray bottle, and a third composition comprising sodium carbonate to the end portion of the hair, e.g. with a pump spray bottle, to create a multi-color or rainbow effect with a pink or red color toward the scalp, a purple color in the middle, and a blue color at the end.

As a further illustrative example, a user may apply a first composition comprising an anthocyanin obtained from red cabbage to the entire head of hair and leave the composition on the hair for a leave-in period ranging from about 20 minutes to about 40 minutes, in order to change the color of the hair from the initial hair color to a first hair color which is pink or red. After the leave-in period, the user may rinse the first composition from the hair and optionally wash and/or condition and/or dry the hair. The user will then have pink or reddish hair for a period of time, until a color changing composition is applied to the hair. By way of example, the user may choose to have the entire head of hair be a pink or reddish color on day one, and on day two apply a second composition comprising sodium carbonate to the entire head of hair, e.g. with a pump spray bottle, to have the entire head of hair be a blue color on day two, and so on.

It should be understood that the above-described methods of applying the first composition to the hair first and the second composition to the hair second are exemplary only, and the order of application of the compositions may be altered. Thus, in an alternate embodiment, the same steps as described above could be followed, but with the initial application of the second composition, followed by application of the first composition to the hair. For example, the second composition may be applied to the hair as described above, the hair optionally dried, optionally without rinsing. Subsequently, the first composition may be applied to the hair as described above, optionally with a leave-in period as described above, and the hair optionally rinsed. Optionally, additional amounts of first or second compositions may then be applied to the hair in order to achieve the desired hair color.

In yet a further alternate embodiment, the first and second compositions may be mixed before they are applied to the hair, for example immediately or substantially immediately before, and the mixture then applied to the hair such as in the manner described above or in any known manner of applying hair dye compositions, optionally with or without rinsing. Subsequently, additional amounts of first or second compositions may optionally be applied to the hair in order to achieve the desired hair color.

It has been surprisingly discovered that the systems, compositions, and methods of changing the color of the hair described herein furthermore impart beneficial properties to the hair such as leaving the hair feel softer, silkier, and more moisturized. Additionally, the compositions provide color that lasts typically from 3-5 washes or more, and is stable to (i.e. not degraded by) light and heat, such as from a hair dryer or styling tool. Further, both the first and second compositions are likewise stable to light under storage conditions. Finally, the systems, compositions, and methods described herein provide consumers with the ability to temporarily change the color of their hair quickly, e.g. instantly or substantially instantly, such as within a few seconds or few minutes, and as often as desired, to impart reversible color, and to impart multiple colors to different portions of the hair.

Kits for Changing the Color of the Hair

Kits according to various embodiments of the disclosure comprise at least one first composition and at least one second composition. Optionally, the first and second compositions may be contained in separate containers in the kit. According to further embodiments, the kits may comprise at least one hair color base in one container and at least one pigment in a separate container, which may be mixed by the user at approximately the time of use to form the first composition. In yet further embodiments, the kits may comprise at least one color changing agent in one container and at least one solvent for forming the second composition in a separate container, which may be mixed by the user at approximately the time of use to form the second composition.

The containers may be any form, such as tubes, bottles, sachets, and the like, without limitation. Additional components of the kits may, for example, include a dye brush applicator, gloves, container(s) for mixing, and the like.

It is to be understood that all definitions herein are provided for the present disclosure only.

It to be understood that, as used herein the terms "the," "a," or "an," mean "at least one," and should not be limited to "only one" unless explicitly indicated to the contrary. Thus, for example, reference to "a pigment" includes examples having two or more pigments unless the context clearly indicates otherwise.

Unless otherwise expressly stated, it is in no way intended that any method set forth herein be construed as requiring that its steps be performed in a specific order. Accordingly, where a method does not expressly recite an order to be followed by its steps or it is not otherwise specifically stated in the claims or description that the steps are to be limited to a specific order, it is no way intended that any particular order be inferred.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a method that comprises A+B+C include embodiments where a method consists of A+B+C and embodiments where a method consists essentially of A+B+C. As described, the phrase "at least one of A, B, and C" is intended to include "at least one A or at least one B or at least one C," and is also intended to include "at least one A and at least one B and at least one C."

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints. The term "about" is used herein to indicate a difference of up to +/−10% from the stated number, such as +/−9%, +/−8%, +/−7%, +/−6%, +/−5%, +/−4%, +/−3%, +/−2%, or +/−1%.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The examples that follow serve to illustrate embodiments of the present disclosure without, however, being limiting in nature.

It will be apparent to those skilled in the art that various modifications and variations can be made in the compositions and methods according to the disclosure without departing from the spirit or scope of the invention. Thus, it is intended that the present invention cover the modifications and variations of this invention provided that they come within the scope of the appended claims and their equivalents.

EXAMPLES

The following examples are intended to be non-limiting and explanatory in nature only.

Example 1: Extraction of Pigment

Naturally-derived pigments useful in a first composition according to the disclosure were extracted from red cabbage using the following procedure.

One head of red cabbage (approximately 1.72 kg) was shredded and split into two equal parts. One part was added to 4 L of acidified (1% hydrochloric acid by volume) water, and the other part was added to 4 L acidified (1% hydrochloric acid by volume) ethanol, and both were soaked for approximately 24 hours in a cool, dark location.

The red cabbage was removed from the solutions and leftover particulates removed from each by gravity filtration. Each solution was washed twice with diethyl ether to remove impurities. The aqueous solution was concentrated by boiling at 100° C. The ethanol solution was concentrated under vacuum at 50 mbar. Both solutions yielded thick, maroon-colored slurries containing anthocyanins derived from red cabbage.

Example 2: Preparation of First Compositions

The naturally-derived pigments obtained by the process of Example 1 were used to prepare an exemplary first composition. Approximately 1.5 parts of the exemplary aqueous slurry concentrate were added to 5 parts of the base color composition in Table 1a, and mixed thoroughly.

TABLE 1a

Base Color Composition

| Component | Amount[1] |
|---|---|
| BEHENTRIMONIUM CHLORIDE | 2.054 |
| TRIDECETH-6 | 0.1 |
| FUMARIC ACID | 0.00175 |
| CETRIMONIUM CHLORIDE | 0.02 |
| CHLORHEXIDINE DIGLUCONATE | 0.04 |
| CETYL ALCOHOL | 1 |
| 2-OLEAMIDO-1,3-OCTADECANEDIOL | 0.01 |
| GUAR HYDROXYPROPYLTRIMONIUM CHLORIDE | 0.09825 |
| ISOPROPYL ALCOHOL | 0.468 |
| CETEARYL ALCOHOL | 3.75 |
| C12-15 ALKYL BENZOATE | 0.5 |
| AMODIMETHICONE | 1.14 |
| CITRIC ACID | 0.025 |
| HYDROXYETHYLCELLULOSE | 0.2 |
| WATER | 90.593 |

[1]By weight, relative to the weight of the base composition.

An alternate base color composition that could be used for preparing the first composition according to embodiments of the disclosure is set forth in Table 1b:

TABLE 1b

Alternate Base Color Composition

| Component | Amount[1] |
|---|---|
| 2-OLEAMIDO-1,3-OCTADECANEDIOL | 0.01 |
| CITRIC ACID | 0.025 |
| CETEARYL ALCOHOL | 3.75 |
| CETYL ALCOHOL | 1 |
| HYDROXYETHYLCELLULOSE | 0.2 |
| GUAR HYDROXYPROPYLTRIMONIUM CHLORIDE | 0.1 |
| CHLORHEXIDINE DIGLUCONATE | 0.2 |
| AMODIMETHICONE (and) TRIDECETH-6 (and) CETRIMONIUM CHLORIDE | 2 |
| C12-15 ALKYL BENZOATE | 0.5 |
| BEHENTRIMONIUM CHLORIDE | 2.6 |
| WATER | 89.615 |

[1]By weight, relative to the weight of the base composition.

Example 3: Preparation of Second Compositions

Several exemplary second compositions (3A-3F) were prepared by adding a color changing agent to water and mixing thoroughly, as shown in Table 2:

TABLE 2

Second compositions

| Composition | Color Changing Agent | Amount[2] |
|---|---|---|
| 3A | CITRIC ACID | 1.88 |
| 3B | SODIUM PHOSPHATE MONOBASIC | 1.17 |
| 3C | SODIUM CITRATE | 2.51 |
| 3D | SODIUM PHOSPHATE DIBASIC | 1.39 |
| 3E | SODIUM BICARBONATE | 0.83 |
| 3F | SODIUM CARBONATE | 1.03 |

[2]The second compositions were prepared with q.s. water to 100%, with the amount being percent weight of the color changing agent.

Example 4: Methods for Changing the Color of the Hair Using the Systems and Compositions of the Disclosure The first composition according to Example 2 (Table 1a) was applied to previously bleached locks of either light brown (previously lightly bleached) or blonde (previously highly bleached) colored hair using a hair dye applicator brush. The first composition was left on the hair for 30 minutes, after which the hair was rinsed, washed, and dried. After the hair was dried, it was noted that the color of the hair had changed from the initial hair color (light brown or blonde) to a first hair color (bright pink).

Subsequently, each of compositions 3A-3F was introduced into individual spray bottles. The dried locks of hair were then sprayed with one of compositions 3A-3F, which caused the color of the locks of hair to change from a first color (bright pink) to a second color, as described in Table 3:

TABLE 3

Color of Hair After Application of Second Composition

| Composition | Color Changing Agent | Color |
|---|---|---|
| 3A | CITRIC ACID | Alternate bright pink color |
| 3B | SODIUM PHOSPHATE MONOBASIC | Alternate bright pink color |
| 3C | SODIUM CITRATE | Pinkish-purple |
| 3D | SODIUM PHOSPHATE DIBASIC | Purple |
| 3E | SODIUM BICARBONATE | Bright teal |
| 3F | SODIUM CARBONATE | Bright blue |

Example 4 demonstrates that the systems, compositions, and methods according to the disclosure provide a fast, convenient, and customizable way to change the color of the hair.

Example 5: Wash Resistance

The locks of hair in Example 5 were washed with shampoo, conditioned, and dried with a hair drier (one (1) wash cycle) five (5) times. After each cycle, the color remaining on each lock of hair, relative to the original color (wash cycle "0", rated 10), was evaluated, as shown in Table 4:

TABLE 4

Color Remaining in Hair After Wash Each Cycle

| | | Wash Cycle | | | | | |
|---|---|---|---|---|---|---|---|
| Composition | Color Changing Agent | 0 | 1 | 2 | 3 | 4 | 5 |
| 3A | CITRIC ACID | 10 | 7 | 5 | 3 | 2 | 1 |
| 3B | SODIUM PHOSPHATE MONOBASIC | 10 | 7 | 5 | 3 | 2 | 1 |
| 3C | SODIUM CITRATE | 10 | 5 | 4 | 3 | 1 | 0.5 |
| 3D | SODIUM PHOSPHATE DIBASIC | 10 | 5 | 3 | 2 | 1 | 0 |
| 3E | SODIUM BICARBONATE | 10 | 7 | 5 | 3 | 2 | 1 |
| 3F | SODIUM CARBONATE | 10 | 7 | 5 | 3 | 2 | 1 |

As can be seen in Table 4, the color on the hair was temporary, lasting through about 4-6 washes.

The invention claimed is:

1. A system for changing the color of the hair, comprising:
   (i) a first composition comprising at least one pigment, and
   (ii) a second composition comprising at least one color changing agent,
   wherein the at least one pigment is capable of imparting a first color to the hair that can be changed to a second hair color by the color changing agent of the second composition, and
   wherein the pH of the first and second compositions are different; and
   wherein the at least one pigment comprises at least one anthocyanin.

2. The system of claim 1, wherein the at least one pigment is chosen from cyanidin, delphinidin, malvidin, pelargonidin, peonidin, or petunidin.

3. The system of claim 1, wherein the at least one anthocyanin is chosen from cyanidin-3-diglucoside-5-glucoside, optionally acylated with p-coumaric, ferulic, or sinapic acids, or combinations thereof.

4. The system of claim 1, wherein the at least one anthocyanin is derived from a natural source.

5. The system of claim 4, wherein the at least one anthocyanin is derived from radishes, purple sweet potatoes, apples, blueberries, raspberries, cranberries, red cabbage, strawberries, eggplant, beets, cherries, curry powder, grapes, onions, peaches, pears, plums, radishes, tomatoes, oranges, purple corn, lingonberries, olives, or turnips.

6. The system of claim 1, wherein the at least one pigment is present in the first composition in an amount ranging from about 0.001% to about 10% by weight, relative to the total weight of the first composition.

7. The system of claim 1, wherein the pH of the first composition ranges from about 3 to about 4.

8. The system of claim 7, wherein the pH of the first composition is about 3.5.

9. The system of claim 1, wherein the at least one color changing agent is chosen from mineral salts, alkali metal phosphates and carbonates, alkali metals of carboxylates, mineral or organic acids, or combinations thereof.

10. The system of claim 9, wherein the at least one color changing agent is chosen from citric acid, sodium phosphate monobasic, sodium citrate, sodium phosphate dibasic, sodium bicarbonate, sodium carbonate, or combinations thereof.

11. The system of claim 1, wherein the at least one color changing agent is present in the second composition in an amount ranging from about 0.001% to about 10% by weight, relative to the total weight of the second composition.

12. The system of claim 1, wherein the first composition and/or second composition comprise at least one additional component chosen from cationic surfactants, nonionic surfactants, cationic polymers, fatty compounds, amino silicones, thickeners, solvents, pH adjusters, preservatives, conditioning agents, or combinations thereof.

13. A method for changing the color of the hair, comprising:
(i) applying a first composition comprising at least one pigment to the hair, and
(ii) applying a second composition comprising at least one color changing agent to the hair,
wherein the hair is rinsed after the application of the first composition and before the application of the second composition,
wherein the at least one pigment is capable of imparting a first color to the hair that can be changed to a second hair color by the color changing agent of the second composition, and
wherein the pH of the first and second compositions are different.

14. The method of claim 13, wherein the first composition is left on the hair for a period of time ranging from about 5 to about 60 minutes before it is rinsed.

15. The method of claim 13, wherein the at least one pigment is chosen from at least one anthocyanin.

16. The method of claim 15, wherein the at least one pigment is chosen from cyanidin, delphinidin, malvidin, pelargonidin, peonidin, or petunidin.

17. The method of claim 15, wherein the at least one anthocyanin is chosen from cyanidin-3-diglucoside-5-glucoside, optionally acylated with p-coumaric, ferulic, or sinapic acids, or combinations thereof.

18. The method of claim 15, wherein the at least one anthocyanin is derived from a natural source.

19. The method of claim 18, wherein the at least one anthocyanin is derived from radishes, purple sweet potatoes, apples, blueberries, raspberries, cranberries, red cabbage, strawberries, eggplant, beets, cherries, curry powder, grapes, onions, peaches, pears, plums, radishes, tomatoes, oranges, purple corn, lingonberries, olives, or turnips.

20. The method of claim 13, wherein the at least one pigment is present in the first composition in an amount ranging from about 0.01% to about 10%, relative to the total weight of the first composition.

21. The method of claim 13, wherein the pH of the first composition ranges from about 3 to about 4.

22. The method of claim 21, wherein the pH of the first composition is about 3.5.

23. The method of claim 13, wherein the at least one color changing agent is chosen from mineral salts, alkali metal phosphates and carbonates, alkali metals of carboxylates, or mineral or organic acids.

24. The method of claim 23, wherein the at least one color changing agent is chosen from citric acid, sodium phosphate monobasic, sodium citrate, sodium phosphate dibasic, sodium bicarbonate, and sodium carbonate.

25. The method of claim 13, wherein the at least one color changing agent is present in the second composition in an amount ranging from about 0.01% to about 10%, relative to the total weight of the second composition.

26. The method of claim 13, wherein the first composition and/or second composition comprise at least one additional component chosen from cationic surfactants, nonionic surfactants, cationic polymers, fatty compounds, amino silicones, thickeners, solvents, pH adjusters, preservatives, and conditioning agents.

27. A kit comprising:
(i) a first container comprising a first composition comprising at least one pigment, and
(ii) a second container comprising a second composition comprising at least one color changing agent,
wherein the at least one pigment is capable of imparting a first color to the hair that can be changed to a second hair color by the color changing agent of the second composition, and
wherein the pH of the first and second compositions are different; and
wherein the at least one pigment comprises at least one anthocyanin.

28. A system for changing the color of the hair, comprising:
(i) a first composition comprising:
(a) at least one anthocyanin chosen from cyanidin-3-diglucoside-5-glucoside, optionally acylated with p-coumaric, ferulic, or sinapic acids, or combinations thereof,
(b) at least one solvent chosen from water and organic solvents, and
(c) optionally at least one additional component chosen from cationic surfactants, nonionic surfactants, cationic polymers, fatty compounds, amino silicones, thickeners, solvents, pH adjusters, preservatives, conditioning agents, or combinations thereof; and
(ii) a second composition comprising:
(a) at least one color changing agent chosen from citric acid, sodium phosphate monobasic, sodium citrate, sodium phosphate dibasic, sodium bicarbonate, sodium carbonate, or combinations thereof; and
(b) at least one solvent chosen from water and organic solvents,
wherein the at least one pigment is capable of imparting a first color to the hair that can be changed to a second hair color by the color changing agent of the second composition, and
wherein the pH of the first and second compositions are different.

* * * * *